(12) United States Patent
Teshima et al.

(10) Patent No.: US 6,207,707 B1
(45) Date of Patent: *Mar. 27, 2001

(54) METHOD FOR CONTROLLING TERMITES

(75) Inventors: Hayato Teshima, Toyonaka; Takaaki Itoh, Nishinomiya, both of (JP)

(73) Assignee: Sumitomo Chemical Company, Limited, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/056,882

(22) Filed: May 5, 1993

(30) Foreign Application Priority Data

Jul. 15, 1992 (JP) .................................. 4-188044
Jul. 15, 1992 (JP) .................................. 4-188045

(51) Int. Cl.$^7$ ................................... A01N 53/00
(52) U.S. Cl. ................................... 514/531
(58) Field of Search ........................... 514/531

(56) References Cited

U.S. PATENT DOCUMENTS 4,276,308  6/1981  Ito et al. .

FOREIGN PATENT DOCUMENTS 63-270610  11/1988  (JP) .

OTHER PUBLICATIONS

Joyce et al, vol. 109, (1988), 109:144, 583; Chemical Abstracts.*

Pesticide Science, 8, 284–290, 1977.

\* cited by examiner

*Primary Examiner*—Allen J. Robinson

(57) ABSTRACT

Termite controlling composition is provided, which has an excellent residual effect and is suitable for applying to soil. The composition comprises (i) at least one pyrethroid compound selected from the group consisting of α-cyano-3-phenoxybenzyl 2-(4-chlorophenyl)-3-methylbutyrate and 3-(2,2-dihalovinyl)-2,2-dimethylcyclopropanecarboxylic acid 3-phenoxybenzyl alcohol ester, the alcohol of which may have a cyano group at a-position and (ii) N-(ethylhexyl)-bicyclo[2.2.1]hept-5-en-2,3-dicarboximide as active ingredient.

3 Claims, No Drawings

METHOD FOR CONTROLLING TERMITES

The present invention relates to a termite-controlling agent and a controlling method thereof.

Hitherto, various termite-controlling agents are known. Generally speaking, when pyrethroid compounds are used as a termite-controlling agent, they are not always satisfactory in the persistence of the efficacy in use for soil treatment, apart from that of the efficacy in use for wood treatment.

The present inventors have extensively studied to find a termite-controlling agent which is superior in the persistence of efficacy, and particularly effective also in use for soil treatment. As a result, the present inventors have found that a composition containing as active ingredients N-(2-ethylhexyl)bicyclo[2.2.1]hept-5-en-2,3-dicarboximide [MGK 264] and at least one pyrethroid compound selected from the group consisting of α-cyano-3-phenoxy-benzyl-2-(4-chlorophenyl)-3-methylbutyrate [fenvalerate] and esters of 3-(2,2-dihalovinyl)-2,2-dimethylcyclopropanecarboxylic acid with a 3-phenoxybenzyl alcohol which may have a cyano group at the α-position (hereinafter this composition is referred to as present composition), is an excellent termite-controlling agent which can solve the above problem. The present inventors thus completed the present invention.

Among the pyrethroid compounds used in the present invention, fenvalerate has four optical isomers. Of these isomers, (S)-α-cyano-3-phenoxybenzyl-(S)-2-(4-chlorophenyl)3-methylbutyrate [esfenvalerate] has the highest termite-controlling activity, so that a higher activity can be expected by using esfenvalerate itself or the isomer mixture containing an increased content of esfenvalerate.

The esters of 3-(2,2-dihalovinyl)-2,2-dimethylcyclopropanecarboxylic acid with 3-phenoxybenzyl alcohol which may have a cyano group at the α-position include for example the following compounds:

3-phenoxybenzyl 3-(2,2-dichlorovinyl) -2,2-dimethylcyclopropanecarboxylate [permethrin], α-cyano-3-phenoxybenzyl 3-(2,2-dichlorovinyl)-2,2-dimethylcyclopropanecarboxylate [cypermethrin] and (S)-α-cyano-3-phenoxybenzyl d-cis-3-(2,2-dibromovinyl)-2,2-dimethylcyclopropanecarboxylate [deltamethrin].

In the present composition, the weight ratio of the pyrethroid compound to MGK 264 is in the range of usually 1:1 to 1:20, preferably 1:2 to 1:8.

The present composition may contain a suitable carrier for formulation in addition to the pyrethroid compound and MGK 264. The proportion of the pyrethroid compound in the composition is usually 0.01 to 50 parts by weight, preferably 0.1 to 20 parts by weight. That of MGK 264 in the composition is usually 0.05 to 50 parts by weight, preferably 0.5 to 30 parts by weight.

The present composition may be formulated by the same method as used in formulation of common insecticides. For example, formulation is carried out as follows: The pyrethroid compound and MGK 264 are dissolved in an organic solvent such as aromatic hydrocarbons, aliphatic hydrocarbons, alicyclic hydrocarbons, alcohols, glycol esters, ketones and esters and if necessary, the resulting solution is fixed to a solid carrier by adsorption; and then auxiliaries for formulation such as emulsifiers, dispersing agents and wetting agents are added therein to formulate into emulsifiable concentrates, oil sprays, wettable powders, dusts, granules, suspension formulations, foaming formulations, spraying formulations, microcapsulated formulations and the like.

Other active ingredients for killing termite, stabilizing agents, preservatives and the like may be incorporated into these preparations.

The present composition has a characteristic that it is effective also in use for soil treatment. The soil treatment is a method of forming a chemicals layer on a soil surface. More specifically, when the liquid formulation is applied, for example, to soil at the underfloor part that men can enter, of wood buildings, it is desirable to apply the liquid formulation with a power-driven sprayer, and particularly to chiefly treat the base of the buildings in which and paths are easily formed. When the liquid formulation is applied to soil at the underfloor part, that men cannot enter, of baths, entrances and the like, a method of making holes in the soil with a drill and injecting the liquid formulation into the holes, is employed.

The amount of the present composition used to control termite varies with treatment methods, preparation forms and other various conditions. Generally, however, the amount used in soil treatment is 1 to 100 $g/m^2$, preferably 5 to 50 $g/m^2$ in the total amount of the pyrethroid compound and MGK 264. In the case of wood treatment, the total amount is 0.1 to 10 $g/m^2$, preferably 1 to 5 $g/m^2$.

The present invention will be illustrated in more detail with reference to the following formulation examples and test examples, but it is not to be interpreted as being limited to these examples alone.

In the examples, all parts are by weight.

FORMULATION EXAMPLE 1

Ten parts of Sorpol SM-200 (a surface active agent produced by Toho Kagaku Co., Ltd.) and 87 parts of xylene are added to 1 part of fenvalerate and 2 parts of MGK 264, and the resulting mixture is thoroughly mixed to obtain an emulsifiable concentrate.

FORMULATION EXAMPLE 2

Ten parts of Sorpol SM-200 and 85 parts of xylene are added to 1 part of fenvalerate and 4 parts of MGK 264, and the resulting mixture is thoroughly mixed to obtain an emulsifiable concentrate.

FORMULATION EXAMPLE 3

Ten parts of Sorpol SM-200 and 81 parts of xylene are added to 1 part of fenvalerate and 8 parts of MGK 264, and the resulting mixture is thoroughly mixed to obtain an emulsifiable concentrate.

FORMULATION EXAMPLE 4

0.25 Part of fenvalerate, 0.5 part os MGK 264, 89 parts of xylene and 97.25 parts of kerosene are mixed to obtain an oil spray.

FORMULATION EXAMPLE 5

0.25 Part of esfenvalerate, 0.5 part of MGK 264, 89 parts of kaolin clay and 10.25 parts of talc are thoroughly pulverized and mixed to obtain a dust.

FORMULATION EXAMPLE 6

Ten parts of Sorpol SM-200 and 85 parts of xylene are added to 1 part of permethrin and 4 parts of MGK 264, and the resulting mixture is thoroughly mixed to obtain an emulsifiable concentrate.

FORMULATION EXAMPLE 7

Ten parts of Sorpol SM-200 and 81 parts of xylene are added to 1 part of permethrin and 8 parts of MGK 264, and the resulting mixture is thoroughly mixed to obtain an emulsifiable concentrate.

FORMULATION EXAMPLE 8

0.25 Part of permethrin, 0.5 part of MGK 264, 2 parts of xylene and 97.25 parts of kerosene are mixed to obtain an oil spray.

FORMULATION EXAMPLE 9

0.25 Part of permethrin, 0.5 part of MGK 264, 89 parts kaolin clay and 10.25 parts of talc are thoroughly pulverized and mixed to obtain a dust.

FORMULATION EXAMPLE 10

Ten parts of Sorpol SM-200 and 85 parts of xylene are added to 1 part of cypermethrin and 4 parts of MGK 264, and the resulting mixture is thoroughly mixed to obtain an emulsifiable concentrate.

FORMULATION EXAMPLE 11

Ten parts of Sorpol 3005 and 85 parts of xylene are added to 1 part of deltamethrin and 4 parts of MGK 264, and the resulting mixture is thoroughly mixed to obtain an emulsifiable concentrate.

TEST EXAMPLE 1

The emulsifiable concentrates obtained in Formulation Examples 1, 2 and 3 were each diluted with distilled water to a predetermined concentration. Five milliliters of every dilute chemicals solution was added to 100 g of sandy loam previously heat-sterilized, and the mixture was thoroughly mixed to prepare a test soil. This test soil was stored at 40° C. under a dark condition. After storage for a predetermined period of time (2 months and 3 months), about 15 g of the test soil was put in a plastic 5 dish (diameter, 9 cm; height, 2 cm) and wetted. Twenty workers of Formosan subterranean termites (Coptotermes formosanus) were liberated in the plastic dish. After the dish was kept at room temperature for 3 days, the condition of the termites was observed.

For comparison, the same test was also carried out using each of fenvalerate and MGK 264. The results are shown in Table 1.

TABLE 1

| Chemicals | Concentration (ppm) | Mortality (%) after 3 days | |
|---|---|---|---|
| | | Storage for 2 months | Storage for 3 months |
| MGK 264 | 500 | 0 | 0 |
| | 1000 | 0 | 0 |
| Fenvalerate | 125 | 0 | 0 |
| | 250 | 0 | 0 |
| Fenvalerate + | 125 + 500 | 100 | 100 |

TABLE 1-continued

| Chemicals | Concentration (ppm) | Mortality (%) after 3 days | |
|---|---|---|---|
| | | Storage for 2 months | Storage for 3 months |
| MGK 264 | 125 + 1000 | 100 | 100 |
| | 250 + 500 | 100 | 100 |
| | 250 + 1000 | 100 | 100 |
| No treatment | — | 0 | 0 |

TEST EXAMPLE 2

The same test as in Test Example 1 was carried out using the emulsifiable concentrates obtained in Formulation Examples 6 and 7.

For comparison, the same test was also carried out using each of permethrin and MGK 264. The results are shown in Table 2.

TABLE 2

| Chemicals | Concentration (ppm) | Mortality (%) after 3 days | |
|---|---|---|---|
| | | Storage for 2 months | Storage for 3 months |
| MGK 264 | 500 | 0 | 0 |
| | 1000 | 0 | 0 |
| Permethrin | 125 | 80 | 30 |
| Permethrin + | 125 + 500 | 100 | 100 |
| MGK 264 | 125 + 1000 | 100 | 100 |
| No treatment | — | 0 | 0 |

As the results of Test Examples 1 and 2 show, the present composition is a termite-controlling agent excellent in the persistence of efficacy, and particularly it is extremely effective also in use for soil treatment.

What is claimed is:

1. A method for preventing decomposition of α-cyano-3-phenoxybenzyl-2-(4-chlorophenyl)-3-methylbutyrate in the soil which comprises applying to the soil N-(2-ethylhexyl) bicyclo[2.2.1]hept-5-en-2,3-dicarboximide, together with said α-cyano-3-phenoxybenzyl-2-(4-chlorophenyl)-3-methylbutyrate, in an amount effective to prevent decomposition of said α-cyano-3-phenoxybenzyl-2-(4-chlorophenyl)-3-methylbutyrate for a period of two months or more.

2. A method according to claim 1, wherein the weight ratio of α-cyano-3-phenoxybenzyl-2-(4-chlorophenyl)-3-methylbutyrate to N-(2-ethylhexyl)bicyclo[2.2.1]hept-5-en-2,3-dicarboximide is 1:1 to 1:20.

3. A method according to claim 1, wherein the weight ratio of α-cyano-3-phenoxybenzyl-2-(4-chlorophenyl)-3-methylbutyrate to N-(2-ethylhexyl)bicyclo[2.2.1]hept-5-en-2,3-dicarboximide is 1:2 to 1:8.

* * * * *